United States Patent [19]

Wellinghoff et al.

[11] Patent Number: 5,130,412

[45] Date of Patent: Jul. 14, 1992

[54] ELECTROCHEMICAL DRUG RELEASE AND ARTICLE

[75] Inventors: Stephen T. Wellinghoff; Charles K. Baker, both of San Antonio, Tex.

[73] Assignee: Southwest Research Institute, San Antonio, Tex.

[21] Appl. No.: 598,365

[22] Filed: Oct. 16, 1990

Related U.S. Application Data

[62] Division of Ser. No. 391,282, Aug. 8, 1989, Pat. No. 4,994,023.

[51] Int. Cl.$^5$ .............. C08G 75/18; A01N 25/34; A01N 43/42; A61K 31/54
[52] U.S. Cl. ..................... 528/391; 528/248; 528/422; 528/423; 528/486; 528/487; 424/408; 436/901; 514/224.8; 514/269; 514/270; 514/282; 514/812; 514/959
[58] Field of Search ............. 528/391, 422, 423, 248, 528/486, 487; 424/408; 436/901; 514/224.8, 269, 270, 282, 812, 959

[56] References Cited

U.S. PATENT DOCUMENTS

| | | | |
|---|---|---|---|
| 4,092,162 | 5/1978 | Wright et al. | 528/422 |
| 4,511,492 | 4/1985 | Swedo et al. | 528/422 |
| 4,548,738 | 10/1985 | Jenekhe et al. | 528/248 |
| 4,624,999 | 11/1986 | Jenekhe | 528/248 |
| 4,952,667 | 8/1990 | Shikatani et al. | 528/248 |

*Primary Examiner*—John Kight, III
*Assistant Examiner*—John M. Cooney, Jr.

[57] ABSTRACT

An electrically conducting self-doped carbazole polymer of the formula:

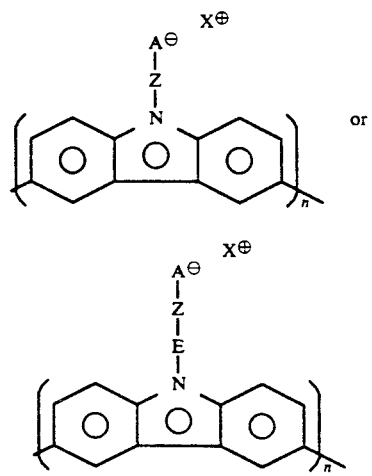

wherein A is a bifunctional molecule capable of bonding to a positively charged molecule at one end and is capable of bonding to a flexible spacer group Z at another end, Z is a flexible spacer group capable of bonding to an anionic group A at one end and is capable of bonding either to a nitrogen or aromatic electron withdrawing or electron donating group at another end, E is a bifunctional molecule capable of bonding to nitrogen at one end and is capable of bonding to a flexible spacer group Z at anther end, X is a positively charged counterion, and n is at least 2.

6 Claims, 1 Drawing Sheet

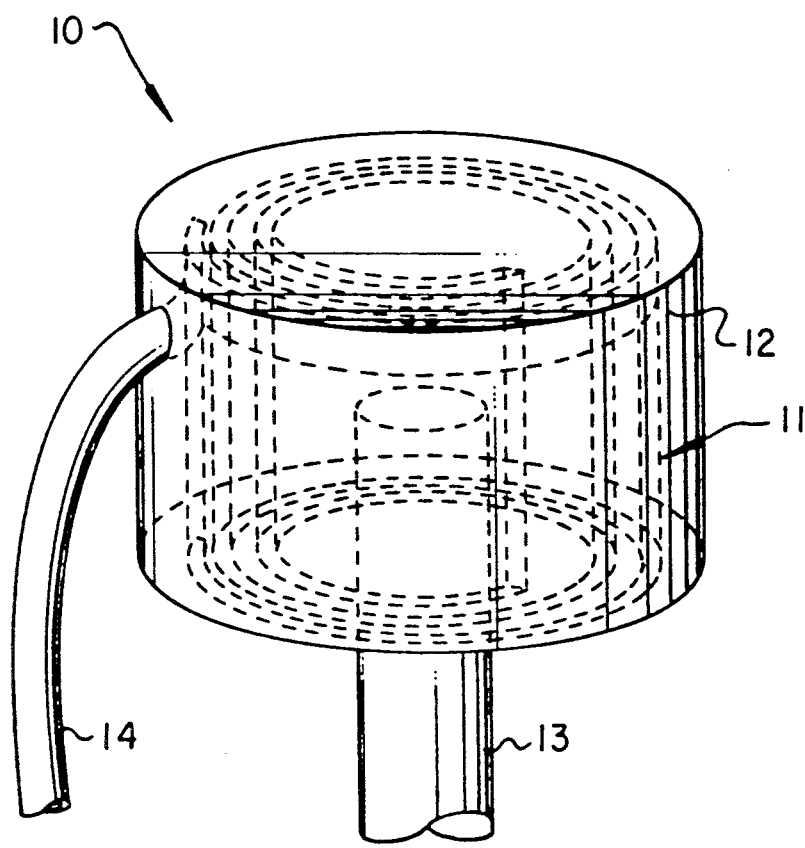

ELECTROCHEMICAL DRUG RELEASE AND ARTICLE

This application is a division of application Ser. No. 391,282, filed Aug. 8, 1989. U.S. Pat. No. 4,994,023.

BACKGROUND OF THE INVENTION

The present invention relates to electroactive carbazole polymers and particularly cationic drug release from such polymers.

Electrochemical methods of drug release have been attempted with the goal of precisely controlling the delivery rate by application of threshold potentials and current flow. In this area of medication an electrically conducting polymer, such as polypyrrole or polythiophene, is usually prepared through electrochemical oxidation to form the oxidized polymer and is electrochemically reduced with a resultant release of a negatively charged counterion which counterion has drug effects.

A drug so released is described in the article by Blankespoor et al in J. Chem. Soc., Chem. Commun., 90 (1985), relative to the release of the glutamate anion which is important in neurotransmission. However, the number of negatively charged drug molecules is quite small in comparison to the number of cationic alkylammonium based drugs which exert powerful effects on the central nervous system. One attempt to achieve cation-specific release involved the use of a polypyrrole/polystyrene sulfonate molecular composite film which was deposited on an electrode by electropolymerizing and oxidizing pyrrole in the presence of the polystyrene sulfonate anion (Miller et al., Macromol., 20,1594 (1987)). This system contained an immobilized dopant anion (polystyrene sulfonate), thus electrochemical reduction of the polymer in the presence of dopamine resulted in adsorption of the drug cation into the polymer film to compensate for the positive charge that had been removed from the polymer chain. The medication could be rereleased by reoxidation of the conducting polymer.

So called, "self-doped", N-alkane sulfonate substituted pyrrole copolymers have become available (Reynolds et al., J. Chem. Soc., Chem. Comm., 620 (1987)) along with 3-alkyl substituted thiophene conducting polymers (Pastil et al., JACS, 109, 1858 (1987)). With these materials, the mechanism of mobile countercation release involves electrochemical oxidation of the polymer backbone to produce a charge compensated polymeric zwitterion. However, once the pyrrole is alkane sulfonated at the nitrogen position steric disturbances force loss of ring planarity and loss of conduction requiring the copolymerization with unsubstituted pyrrole monomer. This acts to limit the total loading of cationic drugs onto the conducting polymer matrix. Thus, for example, polythiophene 3-substituted alkane sulfonates do not have the steric interference problems of the N-substituted pyrroles but do have air and water stability problems.

SUMMARY OF THE INVENTION

The present invention overcomes the problems of the prior art by providing a conducting polymer which is water soluble in both redox states and which provides nitrogen that can be better substituted with groups that modify the solubility and redox potential of the polymer without disturbing the planarity that is essential for electrical conductivity.

Briefly stated, the present invention comprises an electrically conducting self-doped carbazole polymer of the formula:

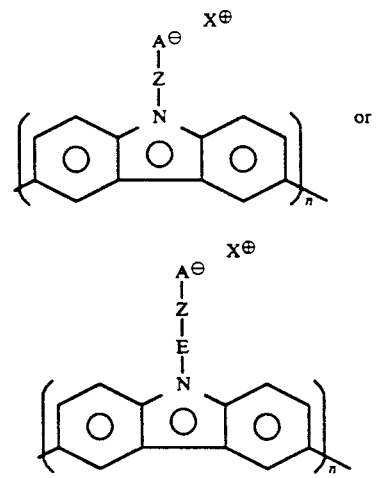

wherein A is a bifunctional molecule capable of bonding to a positively charged molecule at one end and is capable of bonding to a flexible spacer group Z at another end, Z is a flexible spacer group that is a bifunctional molecule capable of bonding to an anionic group A at one end and is capable of bonding to either a nitrogen or electron donating or electron accepting molecule at another end, E is a bifunctional molecule capable of bonding to a nitrogen at one end and is capable of bonding to a flexible spacer group at another end, X is a positively charged cation, and n is at least 2.

The purpose of E is to control the electron density at the carbazole nitrogen and thus the optical and electronic characteristics of the carbazole polymer backbone. The purpose of A is to provide a covalently bound counteranion (know as the dopant ion) which is necessary to stabilize the positive sites along an oxidized carbazole polymer backbone and thus limit ion mobility to cations (X+) during a change in carbazole polymer backbone oxidation state. In addition, the interactions of A with X+ and solvent control the solubility of the carbazole polymer. The purpose of Z is to decouple the electronic structure of A from that of E and the carbazole polymer.

The invention also comprises the drug wherein the positively charged molecule is a positively charged drug molecule as well as the drug delivery device as hereinafter set forth.

BRIEF DESCRIPTION OF THE DRAWING

The single figure of the drawing is a perspective view of a drug delivery device of the present invention with inner portions shown in dotted line which can be implanted in humans and animals for electrochemically controlled drug release.

DETAILED DESCRIPTION

While the instant invention is suitable for use with any cationic drug, it will be described in particularity with respect to the model drug benzyltriethylammonium chloride (BTEA Chloride).

As to the polycarbazole backbone conducting polymers, they can be any electroactive carbazole polymer which is N-substituted by a flexible spacer group and the terminal counteranion without inducing steric interferences at the diaryl bond or by an electron donating or accepting groups, flexible spacer, and terminal counteranion to change the oxidation potential of the polymers without inducing steric interferences at the diaryl bond. Oxidized carbazole polymers also appear to be relatively stable in water and air provided that they are not oxidized beyond the first oxidation wave (0.6 V vs SCE).

The particular electron donating or withdrawing groups can be any bifunctional compound which can react with the nitrogen group on the carbazole with one end and with the flexible spacer group drug at the other end. Examples of suitable aromatic electron withdrawing or electron donating groups include furans, pyrroles, thiophenes, pyrimidines, vinyl benzenes, and the like known electron donating or withdrawing groups with a flexible spacer and bonded to the carbazole nitrogen. An electron withdrawing group will increase the oxidation potential of the polycarbazole while electron donating group will decrease the oxidation potential. In contrast with pyrrole and thiophene polymers, the instant carbazoles can be easily substituted without causing any disturbance of ring planarity and loss of electrical conductivity.

The particular flexible spacer groups can be any bifunctional molecule which can react with either the nitrogen group on the carbazole and/or the electron donating/withdrawing group on one end and with an anionic group on the other. Examples of suitable flexible spacers include methylene, $(-CH_2-)_n$, and ether, $(-ROR-)$, groups. The particular anionic group can be any bifunctional group which can react with the flexible spacer group on one end and with a cation on the other end. Thus, the anionic group can serve as a dopant ion when the polycarbazole is oxidized and as an ionic salt when the polycarbazole is in the neutral state. Examples of anionic groups include sulfonates and carboxylates. Examples of assembled A, Z, and E groups are set forth below with "PB" denoting the carbazole polymer backbone and Y denoting a $(-CH_2-)_n$ group with n equal to at least 1, but preferably 3 or 4, or a $(-ROR-)$ group with R being a $C_1$ to $C_4$ alkylene group.

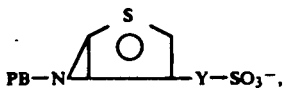

(1)

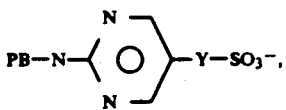

(2)

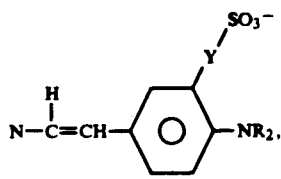

(3)

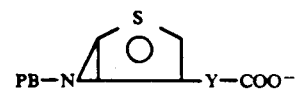

(4)

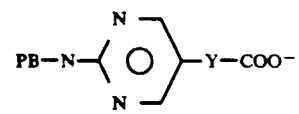

(5)

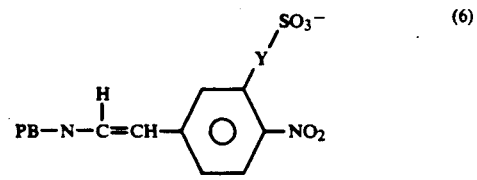

(6)

In formula (1) and (4) the sulfur in the ring can be replaced by oxygen and in formula (6) the $-NO_2$ group can be replaced by any electron withdrawing group, such as CN.

With respect to the drugs that can be utilized, all are cationic drug with examples being the hydrochlorides of cocaine and cocaine derivatives, barbituates and phenothiazenes, antipyrine, morphine, codeine, and other alkaloids, analeptics such as strychnine, adrenergics such as adrenaline, adrenergic blocker, cholinergic blockers such as prostigmine, diphenylhydramine or other antihistamines, and tertiary ammonium salts of anticholonerics such as curare.

The self-doped polymers are made by first forming the monomers. For example, the carbazole monomers can be synthesized by reacting either the carbazole (CZ) or diiodacarbazole (DICZ) with NaH in dimethylformamide (DMF) to form the sodium salt. Before or after ion exchange of the salt with the model drug noted above, namely BTEA chloride, the desired carbazole or diiodocarbazole can be made by reacting with a sultone.

The polymer can be a dimer, or one where n is 10 to 30 or even higher.

The polymerization of the diiodocarbazole monomers can be effected using nickel activated aryl-coupling as set forth in Matsumoto et al. article J. Org. Chem. 48, 840 (1983). Utilizing this technique eliminates the requirement for Grignard-stable solvents that are usually poorer solvents for the polymer. The polymer can also be obtained by polymerizing from acetonitrile solutions containing only the monomer and from solutions containing a monomer and a supporting electrolyte directly onto the electrodes surface by applying an oxidative potential. This electropolymerization method can be effected by constant or pulsed current, constant or pulsed potential, and cyclic potential methods using a two (anode/cathode) or three (working, counter, and reference) electrode cell configuration. Ion release from the film can be monitored gravimetrically by a quartz crystal microbalance working electrode. A resonance frequency decrease for the quartz crystal is indicative of a mass increase in the film and visa versa for a mass decrease.

Referring to the drawing, there is shown a drug delivery device 10 comprising a film 11 of drug loaded conductive polymer. The film 11 is embedded in a biodegradable gel electrolyte 12 with anode electrode 13 and flexible cathode 14 affixed to the device 10. This device can be embedded under the skin and powered by a source on the exterior of the skin. Not shown is the source of external power which can be any conventional source, such as a battery. If necessary, a three electrode arrangement can be employed for better control of electrical potential.

It will be evident that the device can be of any size and can be small enough to be implanted under the skin of human or other animal for continued release of the drug contained in the conductive polymer. The rate of drug release is dependent upon that desired and is easily regulated since for each coulomb applied there will be the release of one drug molecule affixed to a nitrogen in the polymer chain. The rate of solubility of the particular drug loaded of conductive polymer can also be regulated so as to conform to the rate of dissolution of the biodegradable electrolyte. Thus, when the drug molecules are all expended, the polymer and electrolyte can be essentially dissolved and one need only then remove the anode and cathode wires in the same manner as stitches after surgery. This eliminates any need for surgery to remove any device. It will be seen that this is an effective and efficient method for drug delivery.

Also, instead of being in the form of a film, the drug loaded conductive polymer can be in the form of a pellet or other shape. It is necessary only that it not be so thick in any dimension so large as to build up any cell resistance when utilized.

As to the biodegradable gel electrolytes, these are conventional known materials and examples are polyglutamic acid or its copolymers with polyethylene oxide such are disclosed in articles by Petrack et al. Chem. Ind. 19, 45 (1987) and by Sanders in C&E News April 1, p.31 (1985).

The invention will be further described in connection with the following example which is set forth for purposes of illustration only.

EXAMPLE

BTEA 4-(3,6-Diiodocarbazole-9-yl) propane sulfonate (DICZS-BTEA) was prepared by reacting diiodocarbozole (DICZ) with NaH in DMF to obtain the sodium salt. After ion exchange of the salt with the drug benzyltriethyl ammonium chloride (BTEA chloride) the desired dicarbazole, DICZS-BTEA, was made by reacting -propane sultone with the BTEA salt.

The DICZS-BTEA was polymerized through nickel activated aryl-coupling to form the self-doped conducting polymer poly[Benzyltriethylammonium-4-(carbazol-9-yl) propane sulfonate], PSAC, which can be precipitated in the neutral insulating state into acetone. The nonhalogenated carbazole analog was polymerized electrochemically from a 0.30 molar neat solution in acetonitrile directly onto the electrode surface yielding a green, optically transparent film.

The chemically polymerized PSAC was cast as a film onto an electrode surface and can be electrochemically switched to an oxidized state to release the BTEA cations. The amount of BTEA released is controlled by monitoring the number of coulombs passed through the film and the rate of BTEA release is controlled by the oxidation potential applied to the film. The film maybe reloaded with BTEA by switching the polymer film back to the neutral state.

The electrochemically polymerized polymer film has the interesting property that it is insoluble in acetonitrile while in the oxidized state but becomes soluble when neutralized. Thus, for controlled drug release applications, it must be suspended in some media that will help to retain it on the electrode surface when neutral.

The instant self-doped polymeric carbazoles need not have cationic drug counterions. With other counterions films and solutions of these conducting polymers are suitable for sensor protection and optical communications, such as optical limiters, since they have an intensity dependent refractive index as well as intensity dependent adsorption coefficients.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An electrically conducting self-doped carbazole polymer of the formula:

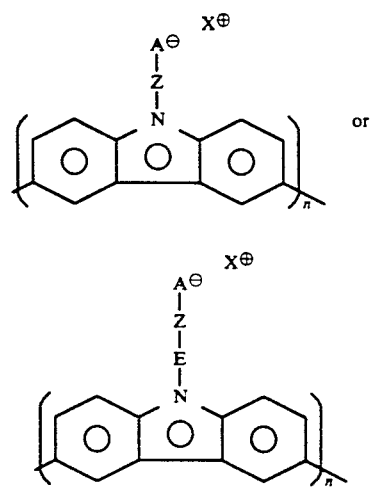

wherein A is a bifunctional molecule capable of bonding to a positively charged molecule at one end and is capable of bonding to a flexible spacer group Z at another end, Z is a flexible spacer group capable of bonding to an anionic group A at one end and is capable of bonding either to a nitrogen or aromatic electron withdrawing or electron donating group at another end, E is a bifunctional molecule capable of bonding to nitrogen at one end and is capable of bonding to a flexible spacer group Z at another end, X is a positively charged counterion, and n is at least 2.

2. The polymer of claim 1 wherein A is a sulfonate or carboxylate, Z is a ($-CH_2-$)$_n$ group with n equal to at least 1 or a ($-ROR-$) group with R being a $C_1$ to $C_4$ alkylene group, E is a furan, pyrrole, thiophene, pyrimidine, or vinyl benzene group, and n is 2 to 100.

3. The polymer of claim 2 wherein X is a cationic drug.

4. A drug comprising an electrically conducting self-doped carbazole polymer of the formula:

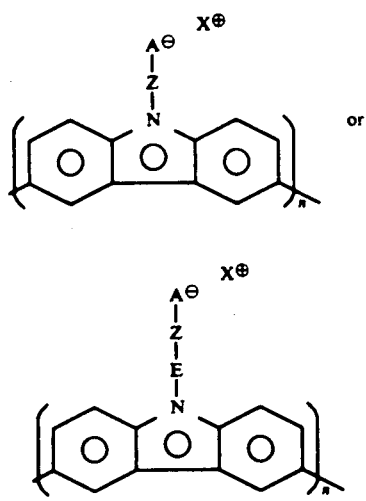

wherein A is a bifunctional molecule capable of bonding to a positively charged molecule at one end and is capable of bonding to a flexible spacer group Z at another and, Z is a flexible spacer group capable of bonding to an anionic group A at one end and is capable of bonding either to an aromatic nitrogen or electron withdrawing or electron donating group at another end, E is a bifunctional molecule capable of bonding to nitrogen at one nd and is capable of bonding to a flexible spacer group Z at another end, X is a positively charged drug molecule, and n is at least 2.

5. The drug of claim 4 wherein A is a sulfonate or carboxylate, Z is a ($-CH_2-$)$_n$ group with n equal to at least 1 or a ($-ROR-$) group with R being a $C_1$ to $C_4$ alkylene group, E is a furan, pyrrole, thiophene, pyrimidine, or vinyl benzene group, and n is 2 to 100.

6. The drug of claim 4 or 5 wherein X is a hydrochloride of cocaine, cocaine derivative, barbituate, phenothiazene, antipyrine, morphine, codeine, analeptic, adrenergic blocker, cholinergic blocker, or tertiary ammonium salt of an anticholinergic.

* * * * *